(12) United States Patent
Francart et al.

(10) Patent No.: US 8,503,704 B2
(45) Date of Patent: Aug. 6, 2013

(54) LOCALISATION IN A BILATERAL HEARING DEVICE SYSTEM

(75) Inventors: Tom Francart, Lane Cove (BE); Jan Wouters, Lane Cove (BE); Bas Van Dijk, Lane Cove (BE)

(73) Assignee: Cochlear Limited (AU)

( * ) Notice: Subject to any disclaimer, the term of this patent is extended or adjusted under 35 U.S.C. 154(b) by 33 days.

(21) Appl. No.: 13/263,407

(22) PCT Filed: Apr. 7, 2009

(86) PCT No.: PCT/AU2009/000437
§ 371 (c)(1),
(2), (4) Date: Dec. 28, 2011

(87) PCT Pub. No.: WO2010/115227
PCT Pub. Date: Oct. 14, 2010

(65) Prior Publication Data
US 2012/0093329 A1    Apr. 19, 2012

(51) Int. Cl.
*H04R 25/00* (2006.01)
(52) U.S. Cl.
USPC .......................... 381/313; 381/312; 381/217
(58) Field of Classification Search
USPC ............ 381/60, 312–313, 315–318, 320–321
See application file for complete search history.

(56) References Cited

U.S. PATENT DOCUMENTS

| 5,870,481 A | 2/1999 | Dymond et al. |
| 2007/0140506 A1 | 6/2007 | Roeck et al. |
| 2008/0013762 A1 | 1/2008 | Roeck et al. |

OTHER PUBLICATIONS van Hoesel et al., "Speech perception, localization, and lateralization with bilateral cochlear implants," J. Acoust. Soc. Am., 2003, vol. 113, No. 3, pp. 1617-1630.
van der Bogaert et al., "Horizontal localization with bilateral hearing aids: Without is better than with," J. Acoust. Soc. Am., Jan. 2006, vol. 119, No. 1, pp. 515-526.
Seeber et al., "Localization ability with bimodal hearing aids and bilateral cochlear implants," J. Acoust. Soc. Am., 2004, vol. 116, No. 3, pp. 1698-1709.
Francart, T., "Perception of binaural localization cues with combined electric and acoustic hearing," Nov. 18, 2008 (PhD Thesis) Library Holding of Katholieke Universiteit Luven, pp. 1-213.
International Search Report for PCT/AU2009/000437 mailed Jun. 19, 2009.

*Primary Examiner* — Suhan Ni
(74) *Attorney, Agent, or Firm* — McDonnell Boehnen Hulbert & Berghoff LLP (57) ABSTRACT

Disclosed is a method and system for allowing a recipient of a hearing aid device, and in one aspect, a bilateral hearing aid system, to locate the source of a sound signal about the recipient. The method uses localization cues in the sound signal and modifies these to provide useable localization cues to generate a stimulating signal for application to the recipient. In one example, a detected localization cue such as an interaural level difference (ILD) is transposed to a lower frequency.

24 Claims, 10 Drawing Sheets

Fig 16

LOCALISATION IN A BILATERAL HEARING DEVICE SYSTEM

CROSS-REFERENCE TO RELATED APPLICATIONS

The present application is a U.S. National Stage Application of PCT Application Number PCT/AU2009000437 filed on Apr. 7, 2009, and currently pending. The entire contents of the PCT/AU2009000437 application are incorporated by reference.

FIELD

The present invention relates to localisation of sound sources in hearing device systems and in one application, to bilateral hearing device systems.

INCORPORATION BY REFERENCE

The following documents are referred to in the present application:
"Perception of binaural localization cues with combined electric and acoustic hearing", PhD Thesis by Tom Francart; Katholieke Univeriteit Leuven, November 2008;
"Amplification of interaural level differences improves sound localization for cochlear implant users with contralateral acoustic hearing", Francart et al, J Acoust Soc Am, 2008d;
US Patent Application No. 2004/0172101 entitled "Peak-Derived Timing Stimulation Strategy For a Multi-Channel Cochlear Implant";
US Patent Application No. 2005/0209657 entitled "Enhancing Cochlear Implants With Hearing Aid Signal Processing Technologies";
U.S. Pat. No. 5,870,481 entitled "Method and Apparatus for Localisation Enhancement in Hearing Aids";
U.S. Pat. No. 5,991,419 entitled "Bilateral Signal Processing Prosthesis"
International Patent Application PCT/EP2008/004959 (WO2008/155123) entitled "Binaural Stimulation in Neural Auditory Prostheses or Hearing Aids";
A localization algorithm based on head-related transfer functions. Macdonald J A. J Acoust Soc Am. 2008 June; 123(6):4290-6;
"Narrow-band sound localization related to external ear acoustics" Middlebrooks J. Acoust. Soc. Am. Volume 92, Issue 5, pp. 2607-2624 (November 1992);
"A New Method For Binaural 3-D Localization Based on HRTFs", Keyrouz et al; ICASSP 2006 pp 341-344.
"Adaptive eigenvalue decomposition algorithm for passive acoustic source localization"; Benesty; J. Accoust. Soc. Am 107 (1), January 2000; pp. 384-391;
Computational auditory scene analysis (2006), ISBN: 978-04-7174109-1 Wang and Brown, chapter 5;
"Time difference of arrival estimation of speech source in a noisy and reverberant environment"; Dvorkind et al; Signal Processing 85 (2005) 177-204;
"Time Delay Estimation in Room Acoustic Environments: An Overview"; Chen et al; EURASIP Journal on Applied Signal Processing; Volume 2006, Article ID 26503, pp 1-19

The entire content of each of these documents is hereby incorporated by reference.

BACKGROUND

Sufferers of hearing loss are, in many cases, able to ameliorate the effects of their hearing loss by the use of hearing devices that amplify surrounding sound signals, couple sound to the inner ear in non-acoustic ways, and/or directly stimulate auditory nerves in the recipient's cochlea, for example, using electrical stimulation.

Examples of such devices include hearing aids, which amplify surrounding signals and provide this to the recipient in the form of amplified acoustic signals (hearing aids may also be implantable), Direct Acoustic Cochlear Stimulation (DACS) systems which convert surrounding sound signals into mechanical actuation signals which stimulate the recipient's cochlea directly, Bone Anchored Hearing Aids (BAHA) which transmit sound from the skull to the cochlea via bone conduction, and cochlear implant systems which convert surrounding sound signals into electrical stimulation signals which are applied directly to auditory nerves inside the recipient's cochlea or inner ear. There are also hybrid systems which provide both mechanical (or acoustic) and electrical stimulation.

In some cases, a recipient will have a hearing device in each ear. This is known as a bilateral system. A bilateral system may consist of a cochlear implant in one ear and a conventional hearing aid in the other ear, a cochlear implant in both ears, a hearing aid in both ears, a hybrid system in both ears, a hybrid system in one ear and a cochlear implant in the other ear, or a hybrid system in one ear and a hearing aid in the other ear. Combinations in which a different system is used in the two ears is known as a bimodal bilateral system.

Even though bilateral hearing device users or recipients will have more chance of detecting the direction of sound than a unilateral user or recipient, bilateral users still suffer from very poor localisation skills compared to normal hearing people. In normal hearing people, location of a sound source is accomplished using a number of different strategies, including using cues such as interaural level difference (ILD), in which the level or magnitude of sound is different in each ear depending upon the location of the source of the sound; and interaural time difference (ITD), in which the sound arrives at each ear at different times, depending upon the location of the source of the sound. Because of the way hearing devices process sound artificially, the usefulness of these cues may be lost or diminished in device users or recipients, making it difficult for the recipient to identify or locate the source of a sound. Furthermore, knowledge of the location of the source of a sound can often assist the recipient in understanding speech in noise.

SUMMARY

According to one aspect of the present invention, there is provided a method of facilitating localisation of a source of a sound signal for a recipient of a bilateral hearing device system comprising a first hearing device and a second hearing device, the method comprising:
receiving the sound signal at the first and second hearing devices;
determining one or more localisation cues in the received sound signal; and processing the determined one or more localisation cues to provide a useable one or more localisation cues; and
generating a stimulation signal representative of the sound signal with the useable one or more localisation cues, for application to the recipient.

In one form, the step of processing the detected one or more localisation cues comprises shifting the detected localisation cue to a lower frequency.

In another form, the step of processing the detected one or more localisation cues comprises amplifying the localisation cue.

In one form, the detected one or more localisation cues is an interaural level difference (ILD).

In another form, the detected one or more localisation cue is an interaural time difference (ITD).

According to a second aspect of the present invention, there is provided a method of facilitating localisation of a source of a sound signal for a recipient of a bilateral hearing device system comprising a first hearing device and a second hearing device, the method comprising:
- receiving the sound signal at the first and second hearing devices;
- detecting an interaural level difference (ILD) in the received sound signal; and
- generating a stimulation signal representative of the sound signal with the detected ILD inserted at a lower frequency, for application to the recipient.

According to a third aspect of the present invention, there is provided a method of facilitating localisation of a source of a sound signal for a recipient of a bilateral hearing device system comprising a first hearing device and a second hearing device, the method comprising:
- receiving the sound signal at the first and second hearing devices;
- detecting one or more localisation cues in the received sound signal; and
- generating a stimulation signal representative of the sound signal with the detected one or more localisation cues amplified, for application to the recipient.

In one form, the localisation cue is an interaural level difference (ILD).

In another form, the localisation cue is an interaural time difference (ITD).

According to a fourth aspect of the present invention, there is provided a method of facilitating localisation of a source of a sound signal for a recipient of a bilateral hearing device system comprising a first hearing device and a second hearing device, the method comprising:
- receiving the sound signal at the first and second hearing devices;
- determining a likely location of the source of the sound signal;
- determining one or more localisation cues for the recipient to perceive the source of the sound signal at the determined likely location; and
- generating a stimulation signal including the determined one or more localisation cues for application to the recipient.

According to a fifth aspect of the present invention, there is provided a bilateral hearing device system for facilitating localisation of a source of a sound signal for a recipient of the bilateral hearing device system comprising a first hearing device and a second hearing device, the bilateral system comprising:
- One or more receivers for receiving the sound signal at the first and second hearing devices;
- means for determining one or more localisation cues in the received sound signal;
- a processor for processing the determined one or more localisation cues to provide a useable one or more localisation cues; and
- a stimulation signal generator for generating a stimulation signal representative of the sound signal with the useable one or more localisation cues, for application to the recipient.

In one form, the processor for processing the determined one or more localisation cues comprises means for shifting the determined one or more localisation cues to a lower frequency.

In one form, the processor for processing the determined one or more localisation cues comprises means for amplifying the determined one or more localisation cues.

In one form, the detected one or more localisation cues is an interaural level difference (ILD).

In one form, the detected one or more localisation cues is an interaural time difference (ITD).

According to a sixth aspect of the present invention, there is provided a bilateral hearing device system for facilitating localisation of a source of a sound signal for a recipient of the bilateral hearing device system comprising a first hearing device and a second hearing device, the bilateral system comprising:
- one or more receivers for receiving the sound signal at the first and second hearing devices;
- a detector for detecting an interaural level difference (ILD) in the received sound signal; and
- a stimulation signal generator for generating a stimulation signal representative of the sound signal with the detected ILD inserted at a lower frequency, for application to the recipient.

According to a seventh aspect of the present invention, there is provided a bilateral hearing device system for facilitating localisation of a source of a sound signal for a recipient of the bilateral hearing device system comprising a first hearing device and a second hearing device, the bilateral system comprising:
- one or more receivers for receiving the sound signal at the first and second hearing devices;
- a detector for detecting one or more localisation cues in the received sound signal; and
- a stimulation signal generator for generating a stimulation signal representative of the sound signal with the detected one or more localisation cues amplified, for application to the recipient.

According to an eighth aspect of the present invention, there is provided a bilateral hearing device system for facilitating localisation of a source of a sound signal for a recipient of the bilateral hearing device system comprising a first hearing device and a second hearing device, the bilateral system comprising:
- one or more receivers for receiving the sound signal at the first and second hearing devices;
- means for determining a likely location of the source of the sound signal;
- means for determining one or more localisation cues for the recipient to perceive the source of the sound signal at the determined likely location; and
- a stimulation signal generator for generating a stimulation signal including the determined one or more localisation cues for application to the recipient.

DRAWINGS

The various aspects of the present invention will now be described in more detail with reference to the following drawings in which.

DETAILED DESCRIPTION

Throughout the following description, the following terms will be used:

"Hearing Device"—this refers to any artificial device that assists the recipient in hearing. This can include a hearing aid that receives surrounding sound signals, amplifies them and provides them to the recipient in the form of amplified acoustic signals (a hearing aid may be partially implanted); Direct Acoustic Cochlear Stimulation (DACS) systems which convert surrounding sound signals into mechanical actuation signals which stimulate the recipient's cochlea or middle ear directly; and cochlear implant systems which convert surrounding sound signals into electrical stimulation signals which are applied directly to auditory nerves inside the recipient's cochlea. There are also hybrid systems which provide both mechanical (or acoustic) and electrical stimulation. Other combinations of the devices mentioned above may also be possible in the future.

"Location"—in this context will be understood to mean a directional location about the recipient and need not include any distance perception from the recipient.

"Useable location cue"—this refers to a location cue that is able to be used by the recipient to assist in determining the location of the source of a sound. The useable location cue may be an amplified version of an existing location cue at the same or similar frequency band, or may be a location cue that is detected or estimated from one frequency band and inserted into a different frequency band, or it may be one type of localisation cue extracted from the signal represented as another type of localisation cue (e.g. ITD represented as ILD). The useable location cue may also include a location cue that is calculated from a separate calculation of the location of the source and inserted into the processed audio signal for application to the recipient.

Figure 1:
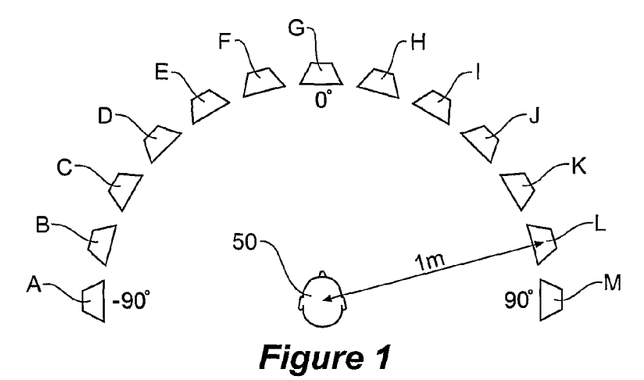
FIG. 1—shows a representation of a person surrounded by a plurality of potential sound sources.

FIG. 1 shows a representation of a recipient 50 surrounded by a plurality of possible sound sources A,B,C, . . . M. As seen in FIG. 1, the location of the source of the sound is accorded a value in terms of degrees. For example, source location A is at −90 deg, source location G is at 0 degrees, and source location M is at 90 degrees. Other source locations (not shown) behind recipient 50 are also possible and will be accorded appropriate angle values. For example, a source location directly behind recipient 50 is at 180 degrees.

The sources of possible sound signals A to M could be target signals such as speech or music, or interfering noise sources such as other speakers, a radio playing or a fan humming.

In normal hearing people, location of a sound source is accomplished using one or more of a number of different strategies, including using cues such as interaural level difference (ILD), in which the level or magnitude of sound is different in each ear depending upon the location of the source of the sound; and interaural time difference (ITD), in which the sound arrives at each ear at different times, depending upon the location of the source of the sound. ITD cues may either be apparent as phase differences in the fine timing structure of a signal (the carrier wave) or as delays in the slow varying envelope of a signal.

In normal circumstances, ILD cues may be as strong as 10-15 dB (depending on frequency) and the smallest ILD that one can detect is in the order of 1 dB. ITD cues may range from 0 to 660 mircoseconds. The smallest detectable value is in the 10 microsecond range.

Figure 2:
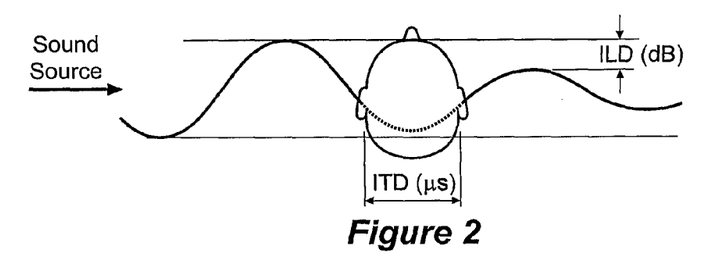
FIG. 2—illustrates the localisation cues of Interaural Level Difference (ILD) and Interaural Time Difference (ITD)

FIG. 2 shows a representation of ILD and ITD in the context of an incoming sound from a source located at location A or at −90 degrees in FIG. 1.

Figure 3:
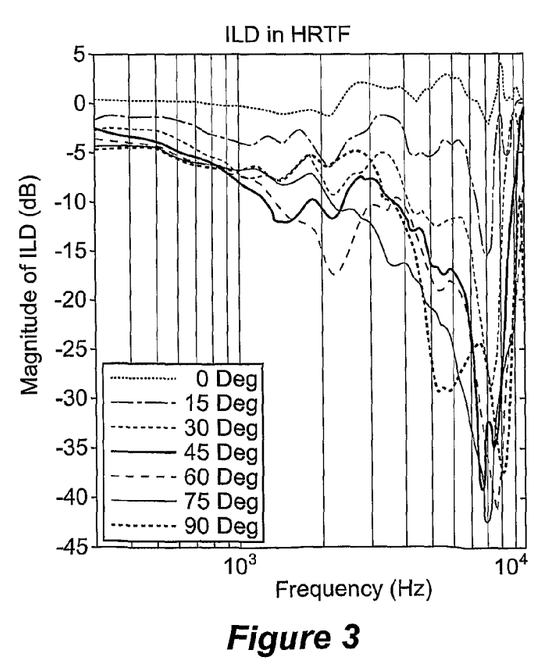
FIG. 3—shows a plot of ILDs for varying source locations.

The ILD is due to head shadow effect, that is, the effect of the head attenuating the sound arriving at the ear behind the head with respect to the source (in FIG. 2, the right ear). For sound sources located more than about 1 meter from the ear, ILDs are considered useful for localisation, at frequencies greater than about 1500 Hz. FIG. 3 shows a plot of ILDs per frequency for different angles of incidence. It can be seen that the magnitude of the ILDs is greatest in the higher frequencies.

Because of the way hearing devices process sound artificially, the usefulness of these cues may be lost or diminished in bilateral recipients, making it difficult for the bilateral recipient to identify or locate the source of a sound. For example, in the case of ITDs, where ITD information is present in the fine structure of the signal, this information is often lost when the device is a cochlear implant because the processor of the cochlear implant removes this fine structure from the incident sound signal and only transmits the per-band slow temporal energy envelopes. Furthermore, in the case of bilateral devices, the two devices are, in general, not synchronised and so time difference information from the ITDs have little meaning. In the case of ILD cues for bimodal recipients, these are not generally available to bilateral recipients because in most bimodal recipients, the residual acoustical hearing is only available at lower frequencies and as previously discussed with reference to FIG. 3, ILDs are most prominent in the higher frequencies.

According to one aspect of the present invention, there is provided a bilateral hearing system in which useable location cues are provided in the lower frequency range of the recipient. It has been discovered by the inventors of the present application (see for example, the paper "Amplification of interaural level differences improves sound localization for cochlear implant users with contralateral bimodal hearing", Francart et al, previously incorporated by reference), that the transposition of ILD cues from the higher frequencies to the lower frequencies can be used by bimodal recipients for localisation. In another example, the useable location cue may be the amplification of the already-existing ILD or ITD information in that lower frequency range.

Figure 4:
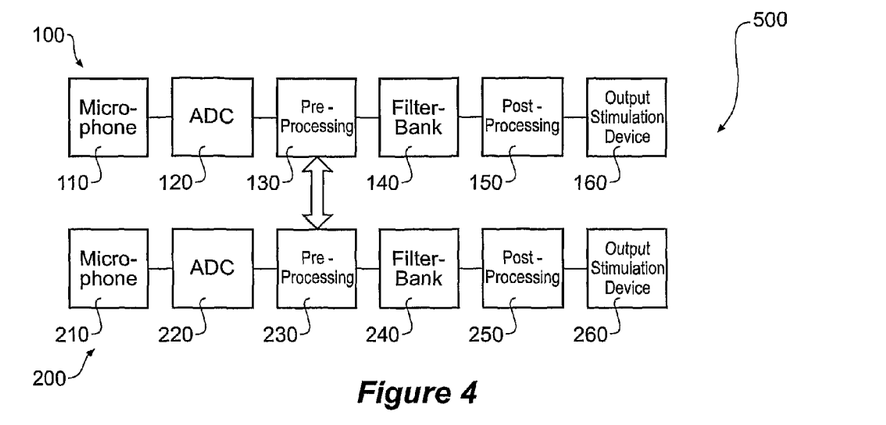
FIG. 4—shows an example of a bilateral system comprising two hearing devices on which the various aspects of the present invention may be employed.

FIG. 4 shows one example of a bilateral hearing system 500 comprising a first hearing device 100 and a second hearing device 200. Hearing device 100 may be a hearing aid (HA), a cochlear implant (CI), a DACS system or a hybrid device. Hearing device 200 may equally be any one of a hearing aid (HA), a cochlear implant (CI), a DACS system or a hybrid device. An example of a CI/CI bilateral system is described in US Patent Application No. 2004/0172101 entitled "Peak-Derived Timing Stimulation Strategy For a Multi-Channel Cochlear Implant", previously incorporated by reference.

In each device 100, 200, there is microphone 110, 210, which captures surrounding sound signals, and provides these to analog-to-digital convertor ADC 120, 220 for converting the analog sound signal into a digital signal for further processing. ADC 120,220 provides the digital signal to pre-processing block 130, 230 for processing. This processing may include sensitivity control or Automatic Gain Control (AGC). As will be understood by the person skilled in the art, the input block described above adapts the signal for use by the rest of the system. An example of a cochlear implant with pre-processing is described in US Patent Application No. 2005/0209657 entitled "Enhancing Cochlear Implants With Hearing Aid Signal Processing Technologies", previously incorporated by reference.

It will be appreciated that non-synchronised input pre-processing between the two devices 100, 200 may result in the loss of location cues. For example, if the sound signal incident on one device is louder than the sound in the other device, the AGC in the louder device may compress the signal more than in the other device, resulting in loss of ILD information. Furthermore, in the case of ITDs, where timing is of paramount importance, unsynchronised processes could result in loss, attenuation, or misrepresentation of ITD information.

FIG. 4 shows that in this example, the pre-processing stages 130,230 communicate with each other to synchronise their respective operations. An example of a bilateral system providing synchronisation between hearing devices is described in U.S. Pat. No. 5,991,419 entitled "Bilateral Signal Processing Prosthesis" previously incorporated by reference. It will be appreciated however, that the two devices need not communicate with each other, and may be synchronised by other means, including pre-setting the various parameters so as to coordinate with each other.

Filterbank 140,240 analyses the frequency content of the sound signal. The post-processor 150,250 may provide any desired post-processing such as an ACE™ strategy for cochlear implants. Finally, the processed signal is applied to an output stimulation device 160,260 for application of the stimulation signal to the recipient. It will be apparent for somebody skilled in the art that the exact architecture of the device as shown in FIG. 4 may differ between devices, for instance a hearing aid need not to have a post processing block 150/250. These differences are not relevant to the various aspects of the present invention. In the case of a hearing aid (HA), the output stimulation device may be a receiver (a receiver is a common term for a loudspeaker in a hearing aid) for providing amplified and processed acoustic stimulation to the eardrum of the recipient. In the case of a cochlear implant (CI), the output stimulation device may be an electrode array for applying electrical stimulation signals directly to the auditory nerves in the cochlea of the recipient. In the case of a DACS device, the output stimulation device may be a mechanical actuator for applying mechanical stimulation to a window of the recipient's cochlea or to one of the auditory bones in the recipient's middle ear.

It will be appreciated that in the case of a hearing implant such as a cochlear implant, a (partially) implanted hearing aid, or a DACS, part of the device will be external to the recipient and part will be internal with communications between the internal and external parts occurring transcutaneously as will be understood by the person skilled in the art. FIGS. 4, 5 and 6 (below) do not show any separation of the two parts as this is not relevant to the various aspects of the present invention.

It will also be appreciated that in the case of a hybrid device, there may be two or more parallel paths, but again these are not shown for the sake of clarity.

Figure 5A:
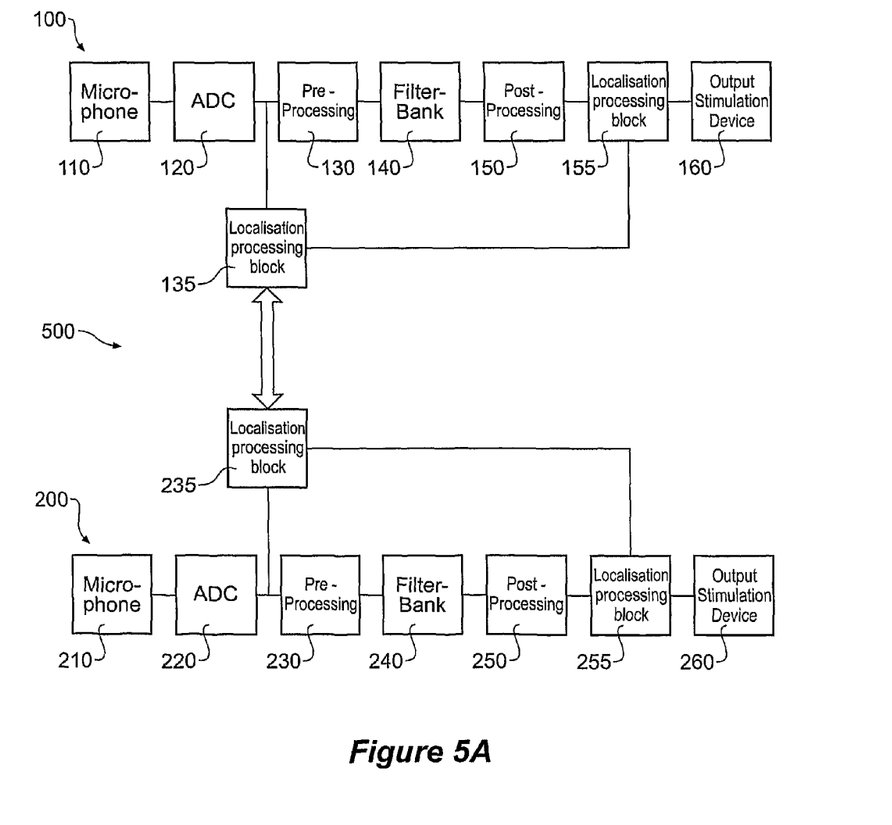
FIG. 5A—shows another example of a bilateral system comprising two hearing devices on which the various aspects of the present invention may be employed.
Figure 6:
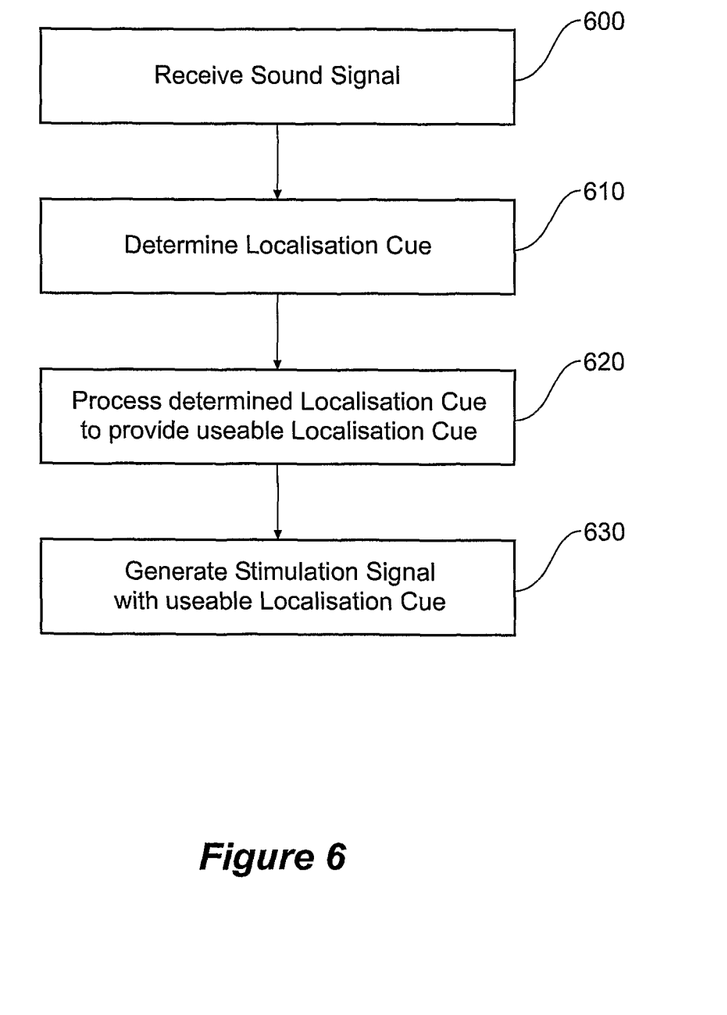
FIG. 6—shows a flowchart of a general method of allowing the recipient to locate the source location.

FIG. 5A shows an alternative arrangement in which part of the pre-processing is shown as including localisation pre-processing as a separate functional block 135. Of course, it will be appreciated that this functionality may be physically provided on the same processor as pre-processing block 130, or indeed as any other processing block. A corresponding localisation pre-processing block 235 in device 200 is also provided. As shown, in this example, these blocks also communicate with each other. This communication channel may be one or more wireless links.

Blocks 135 and 235 may exchange full bandwidth or compressed, uni- or bi-directional audio, but may also or instead, exchange other data such as one or more parameters associated with one or more location algorithms as will be described in more detail below.

Figure 5B:
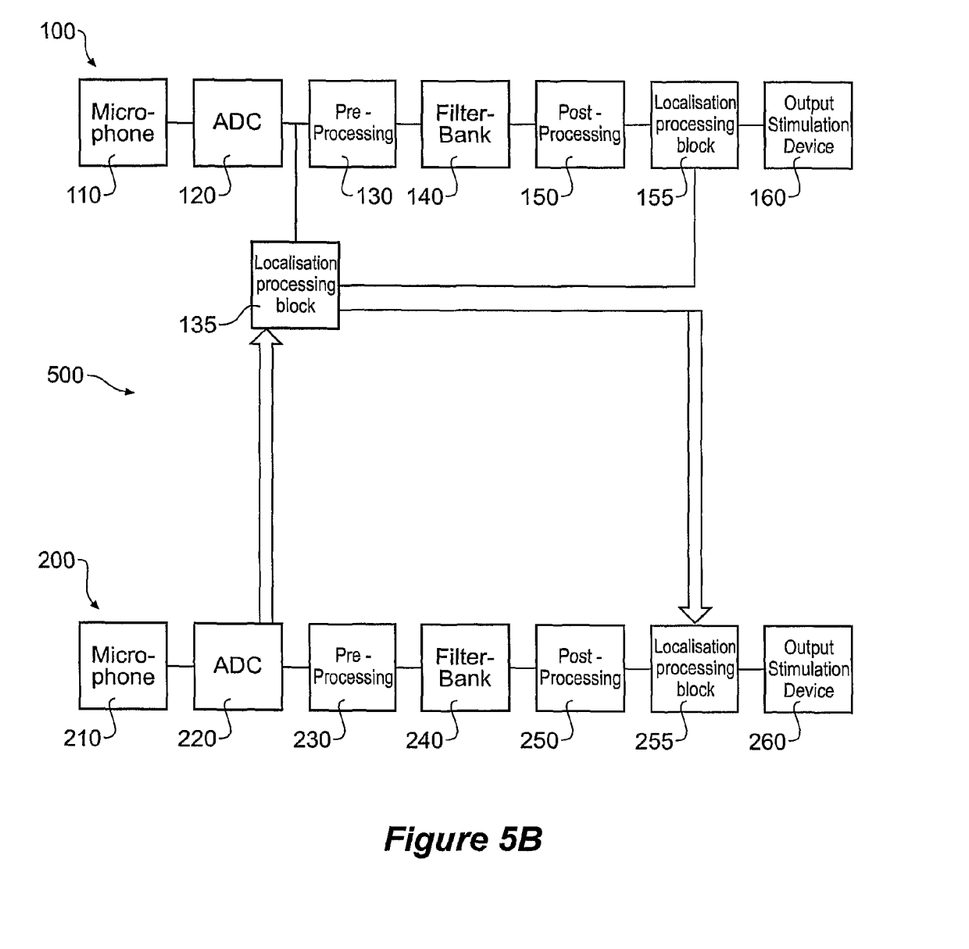
FIG. 5B—shows a further example of a bilateral system comprising two hearing devices on which the various aspects of the present invention may be employed.

FIG. 5B shows yet a further example of an arrangement of a bilateral hearing system 500, comprising two hearing devices 100 and 200, with like parts accordingly labelled. In this arrangement, there is only one localisation pre-processing block 135. In this case, full audio may be streamed to one device. In this arrangement, there is a backwards link between block 220 and block 135 that sends control data back to the 'slave' device to control the output.

In some implementations, one or both devices 100,200 may contain multiple microphones and more than one audio stream may exist to optimize the location algorithms.

In each of the arrangements shown in FIGS. 4, 5A, and 5B, use is made of two algorithms to effect the various aspects of the present invention. The first algorithm, in the pre-processing blocks 130,230 FIG. 4 (or localisation pre-processing blocks 135,235 FIG. 5A, or localisation pre-processing block FIG. 5B), is used to extract or otherwise determine, location data from the input sound signal detected by microphones (110, 210).

Any suitable algorithm may be used. If one or both devices contain more than one microphone, more data streams may be exchanged, but alternatively a device may do some pre-calculations based on its own multiple microphone signals, then exchange a single data stream with the other device that also pre-calculated parameters.

Sum-and-delay type algorithms may be used to estimate the Direction Of Arrival (DOA). Alternatively, autocorrelation type algorithms may be used to estimate the ITD. These algorithms may run on the broadband signals or on sub-band (filtered) versions of the signal.

Algorithms that look at the ratio of energy in a subband over a certain period of time, may also be used, thus estimating ILD cues. When this is done, there is no need to transfer full audio over the link. Instead, sub-band average energies (envelope) signals may be transferred instead to reduce bandwidth. In ILDs the average energy will have a very typical distribution over frequencies due to the head-related transfer function (HRTF). The algorithm may specifically look for spectrally-distributed ILDs that follow the HRTF.

For example, as described in the PhD thesis "Perception of binaural localization cues with combined electric and acoustic hearing", previously incorporated by reference, the inventors have developed an algorithm that makes use of the full-band signals from the microphones of both hearing devices 100,200 (for example HA and CI) (see pages 125,126). If $A_{CI}$ is the root mean square (RMS) amplitude of the signal at the microphone of the CI speech processor, and $A_{HA}$ is the RMS amplitude of the signal at the microphone of the HA, then the ILD in dB is defined as:

$$\text{ILD}=20 \log(A_{CI})-20 \log(A_{HA}) \quad (1)$$

Other examples of suitable localisation algorithms are described in the following documents, all previously incorporated by reference—A localization algorithm based on head-related transfer functions, Macdonald JA. J Acoust Soc Am. 2008 June; 123 (6): 4290-6; "Narrow-band sound localization related to external ear acoustics" Middlebrooks J. Acoust. Soc. Am. Volume 92, Issue 5, pp. 2607-2624 (November 1992); "A New Method For Binaural 3-D Localization Based on HRTFs", Keyrouz et al; ICASSP 2006 pp 341-344; "Adaptive eigenvalue decomposition algorithm for passive acoustic source localization"; Benesty; J. Accoust. Soc. Am 107 (1), January 2000; pp. 384-391; and Computational auditory scene analysis (2006), ISBN: 978-04-7174109-1 Wang and Brown, chapter 5; U.S. Pat. No. 5,870,481 entitled "Method and Apparatus for Localisation Enhancement in Hearing Aids" (describing a method of determining ILDs and use in bilateral hearing aids); and International Patent Application PCT/EP2008/004959 (WO2008/155123) entitled "Binaural Stimulation in Neural Auditory Prostheses or Hearing Aids" (describing a method of determining ITDs and controlling the hearing devices accordingly).

In other examples, localisation cue information may be estimated rather than detected or extracted. Examples of suitable algorithms for estimating localisation cues are—"Time difference of arrival estimation of speech source in a noisy and reverberant environment"; Dvorkind et al; Signal Processing 85 (2005) 177-204; and "Time Delay Estimation in Room Acoustic Environments: An Overview"; Chen et al; EURASIP Journal on Applied Signal Processing; Volume 2006, Article ID 26503, pp 1-19, both previously incorporated by reference.

Once the localisation cues have been detected or estimated in the pre-processing blocks 135,235, the information is used to modify the processed input audio signal in a post-processing stage by blocks 150, 155,250,255 as previously described.

The type of post-processing may vary. The algorithms in the PostLoc block may perform 1 of 2 functions or a combination of both. In general they will, based on the control data input from the PreLoc blocks introduce and/or enhance ILD and/or ITD cues.

In a simple implementation the ILDs found or estimated in higher frequencies in the PreLoc block may simply drive subband gain blocks in the lower frequencies. In this way, ILDs in higher frequencies (which are more prominent) are transferred to ILDs in lower frequencies (more audible for hybrid patients or others with only low-frequency acoustical residual hearing). For example in FIG. 5B, block 135 will transfer control instructions or data to the post-processing blocks 155,255 to implement the modification of the processed signal to generate the stimulation signal for application to the recipient through output stimulation device 160, 260. In this example, all the pre-processing is done in one device (100), and the results transmitted to the other device (200) to generate the appropriate stimulation signal. The first device (100) will simply take the required instructions for generation of its stimulation signal from its own pre-processing block 135.

In alternative implementations, the high frequency ILDs may be amplified, re-tuned, or even made binary. If people have trouble 'hearing' the exact DOA, it could be estimated from the PreLoc block and cues applied that place the signal in front when the direction was −45-45 degrees, to the right if the DOA was 45-135 degrees, to the left when it was −135-−45 degrees, etc. This will lead to less resolution for the recipient but may make it easier to point the recipient's attention to 'about' the right direction. Delay blocks in the processing chain may also be introduced or subband delays may be amplified to transmit ITD cues.

In a further step the amount of ILD or ITD introduced in PostLoc may be recipient-dependent. A method may be implemented of measuring the recipient's sensitivity to ILDs or ITDs and depending on these measurements more or fewer cues could be introduced. This may also be time-variable and re-adjustable.

The following describes a number of methods that may be used in applying the various aspects of the present invention.

FIG. 6 is a flowchart describing a general method of allowing a recipient to locate the source of a sound signal. In step 600, the sound signal is received at the receivers of the devices 100,200. A localisation cue is then determined in step 610. This determination may be done by detecting or measuring a localisation cue in the received signal using one or more of the algorithms or techniques described above. In another example or embodiment, the determination is done by independently calculating the localisation cue from a calculation or estimation of the location of the source of the sound signal and determining the localisation cue from that.

In step 620, the determined location cue is then processed in one or more of a number of ways. In one example, the determined location cue (for example ILD), is shifted or transposed into a lower frequency band. This is described in more detail below with reference to FIG. 7. In another example, the determined localisation cue (for example ILD or ITD) is amplified at its existing frequency band. This method is described in more detail below with reference to FIG. 8. In yet another example, if the localisation cue is determined from an independent calculation or estimation of the location of the source of the sound signal, the processing step involves inserting the determined localisation cue into a stimulation signal to provide the recipient with the required localisation cues so as to be able to perceive the location of the source of the sound signal at the location previously calculated or estimated. This method is described in more detail with reference to FIGS. 9-16.

Figure 7:
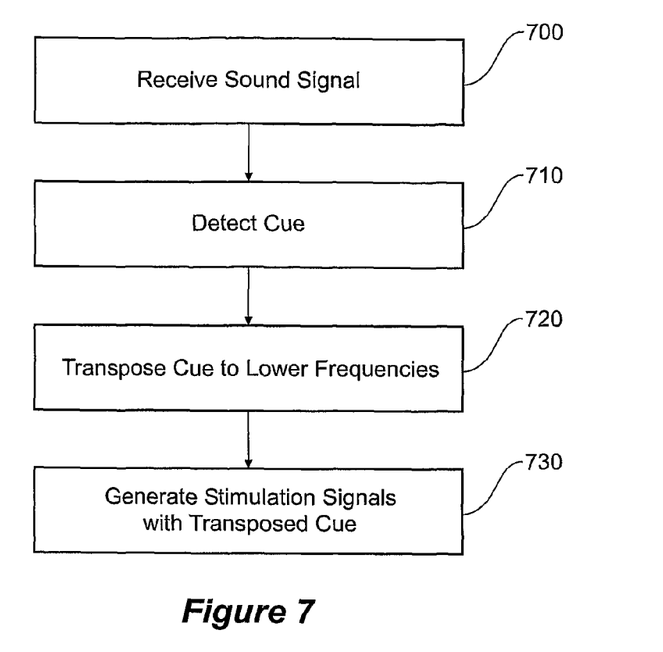
FIG. 7—shows a flowchart for one method of allowing the recipient to locate the source location using frequency-transposed cues.

FIG. 7 is a flowchart of a general method of assisting a recipient in locating the source of a sound using frequency transposition of an ILD. In step 700, the sound signal is received at the microphones of the devices 100,200. The received signal is then processed by one or both devices as previously described and a cue is detected or otherwise identified. This cue may be an ILD for example, and may be identified using any one or more of the various algorithms or techniques previously described. This ILD is likely to be in the higher frequencies of the signal, and not useful to the recipient because of the recipient's hearing condition. Upon further processing, the detected cue (e.g. ILD) is transposed into the lower frequencies, where it is more useable by the recipient. In essence then, the method shown in FIG. 7 comprises receiving a sound signal at the receiver; determining a localisation cue in the received sound signal, and generating a stimulation signal representative of the received sound signal with the useable localisation cue inserted in the stimulation signal.

Figure 8:
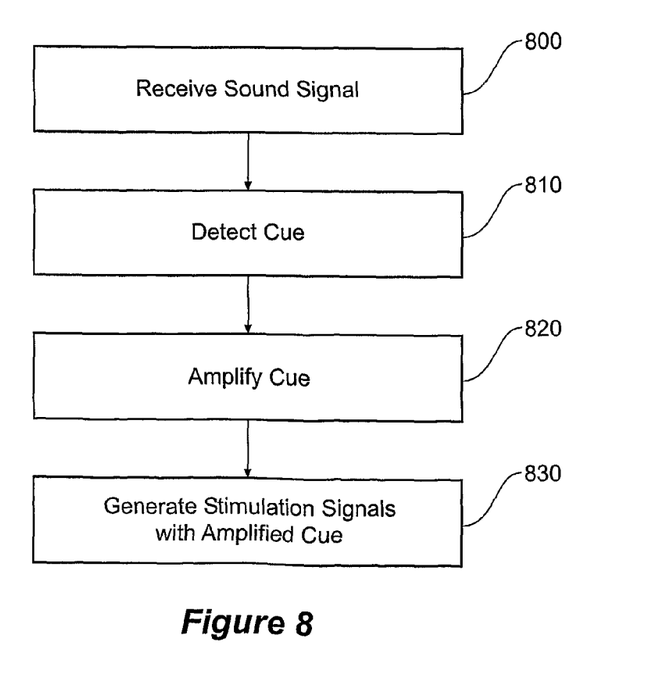
FIG. 8—shows a flowchart for another method of allowing the recipient to locate the source location using amplified cues.

FIG. 8 is a flowchart of a general method of assisting a recipient in locating the source of a sound using frequency amplification of an ILD or ITD. In step 800, the sound signal is received at the receivers of the devices, and in step 810, one or more the localisation cues (for example, ILD and/or ITD) are detected using one or more of the techniques or algorithms described above. In this example, the stimulation signal is generated with the detected localisation cue amplified, thereby inserting a useable localisation cue in the generated stimulation signal. In this case, the localisation cue is not transposed from a higher frequency to a lower frequency, but rather the localisation cue that is present in the lower, useable frequencies, is amplified to be more useable by the recipient.

Figure 9:
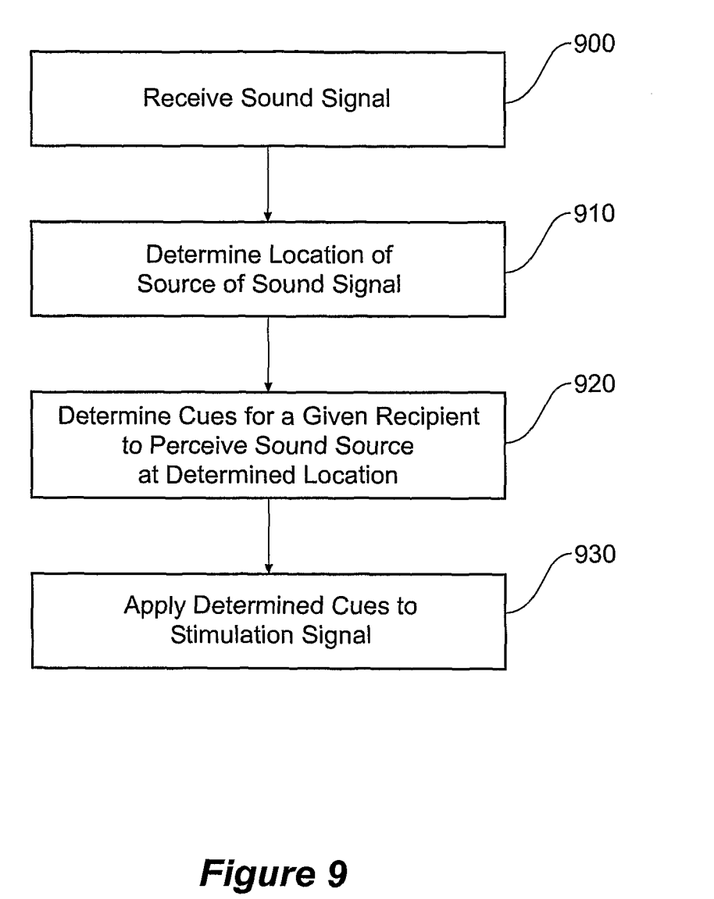
FIG. 9—shows a flowchart of a general method of allowing a recipient to locate the source location using cues determined from a calculation of the likely location.

In another example, as shown in FIG. 9, the useable localisation cues are determined from an independent determination of the location of the sound source and in some cases, may be modified so that the recipient will perceive the location of the sound source to be where is was independently determined. This effectively provides a "mapping function" between the location of the sound source and the ILDs required by the recipient to locate the sound source. This again, provides for the generation of a stimulation signal with a useable localisation cue to allow the recipient to locate the source of the original sound signal. In step 900, the sound signal is received at the receivers of the devices, and in step 910, a determination of the location of the source of the sound signal is made using one or more of the algorithms or techniques described above. In step 920, one or more localisation cues are determined that will allow the recipient to locate the source of the sound signal. In step 930, the stimulation signal is generated with the determined localisation cues, or useable location cues.

Figure 10:
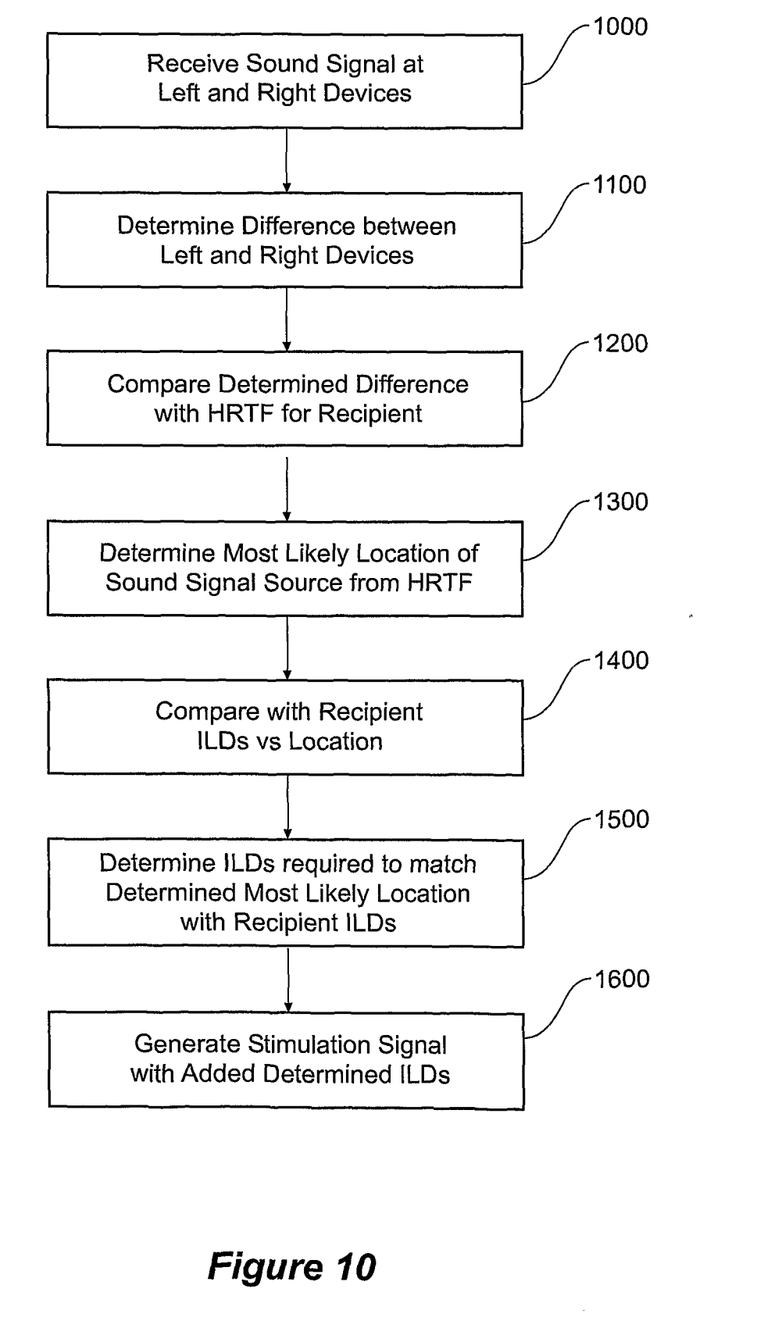
FIG. 10—shows a flowchart of a more detailed method of FIG. 9.

FIG. 10 provides a more detailed flowchart of one method as shown in and described with reference to, FIG. 9 above. In step 1000, the sound signal is received at the left and right devices 100,200. In step 1100, the difference between the signals at the left and right devices is determined. In step 1200, this determined difference is compared with a pre-generated or otherwise known HRTF for the recipient, and a closest match is selected (e.g. by way of a look-up table) and in step 1300, the closest matching HRTF is used to determine the most likely location of the sound signal. In steps 1400 and 1500, the location cues for that recipient that would allow the recipient to perceive the location of the sound signal as the most likely location are determined. This may be done by any suitable means, including referring to a look up table populated with previously-measured data for the recipient. These determined location cues (such as ILDs) are then inserted into the stimulation signal for application to the recipient in step 1600.

Figure 11:
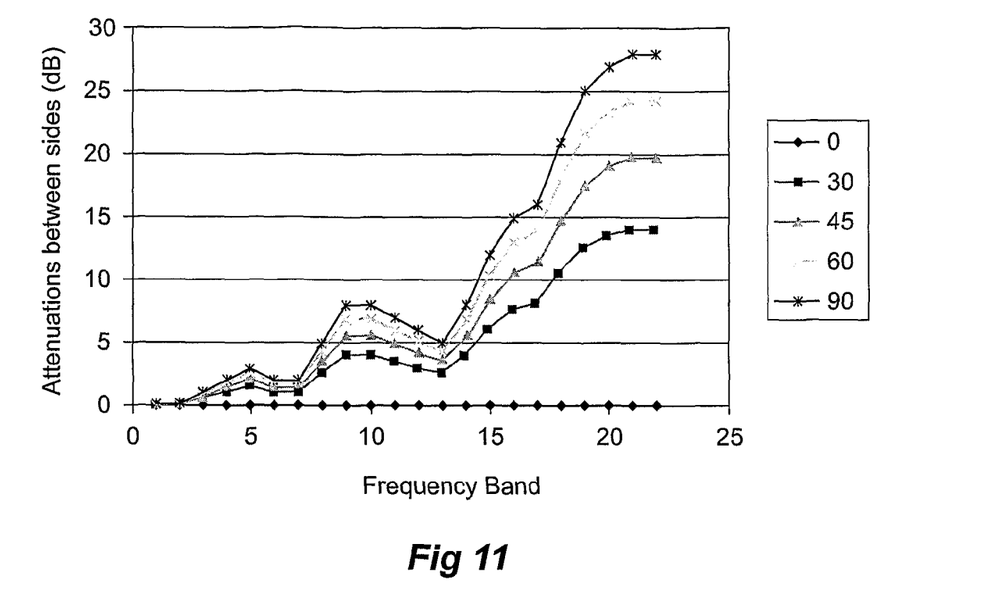
FIG. 11—shows a chart of HRTF for two devices.

The following, with reference to FIGS. 11-16, provides an example of the method shown in FIGS. 9 and 10 above. FIG. 11 shows an HRTF of 2 devices on the recipient's head. The horizontal axis shows frequency bands used in the device (low to high frequency). On the vertical axis the difference in intensity between the left and right microphone is displayed for signal coming from different directions (0 degrees; front, 90 degrees: right side). This HRTF is known or at least known to some approximation.

Figure 12:
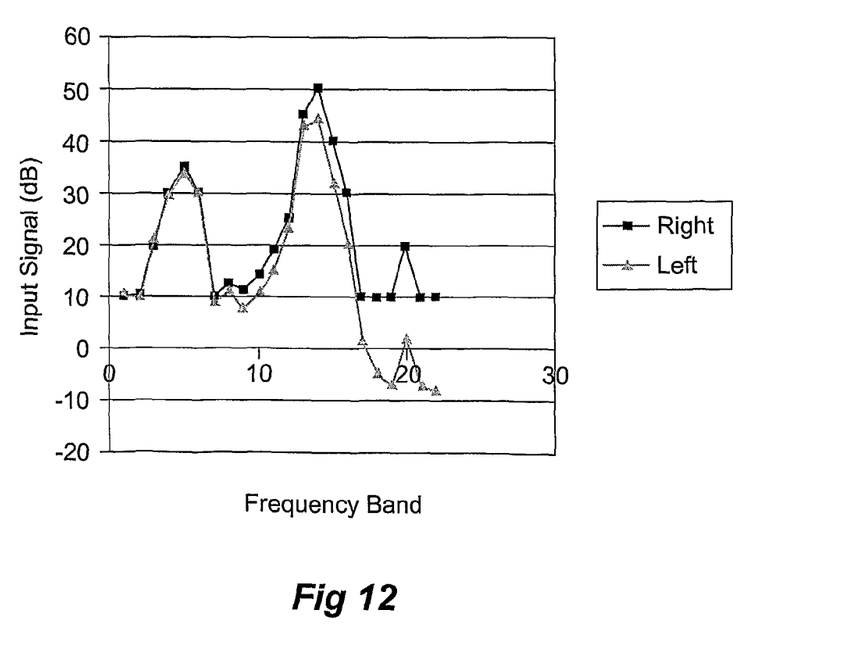
FIG. 12—shows a chart of energy spectrum for the signals at the two devices at a point in time.

FIG. 12 shows, at a certain point in time, the energy spectrum of the left and right input signal.

Figure 13:
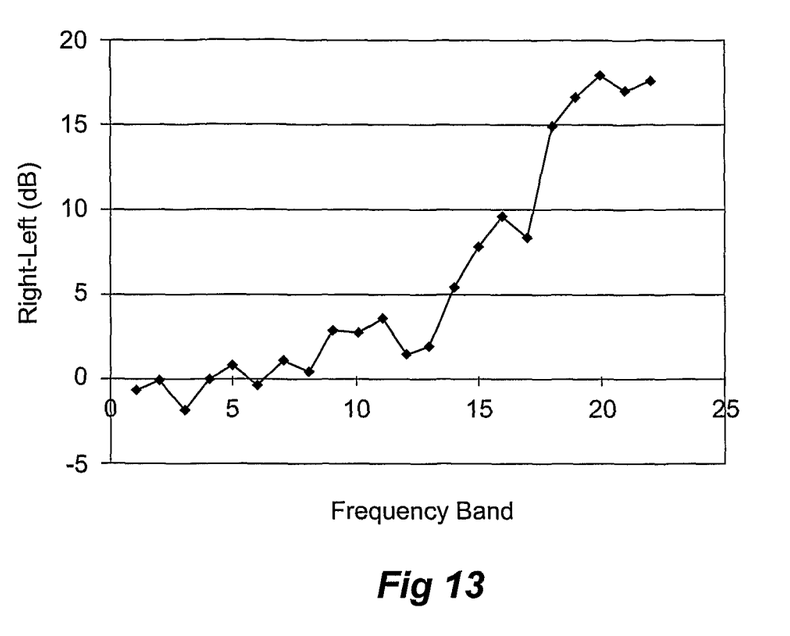
FIG. 13—shows the difference between the left and right signals of FIG. 12.

The difference between the right and left signal per band is shown in FIG. 13. Comparing this difference curve to the HRTFs of the first graph (FIG. 11) the algorithm extracts that the most likely DOA of the most prominent signal is in the order of 45 degrees (for example by comparing ILD magnitudes.

Figure 14:
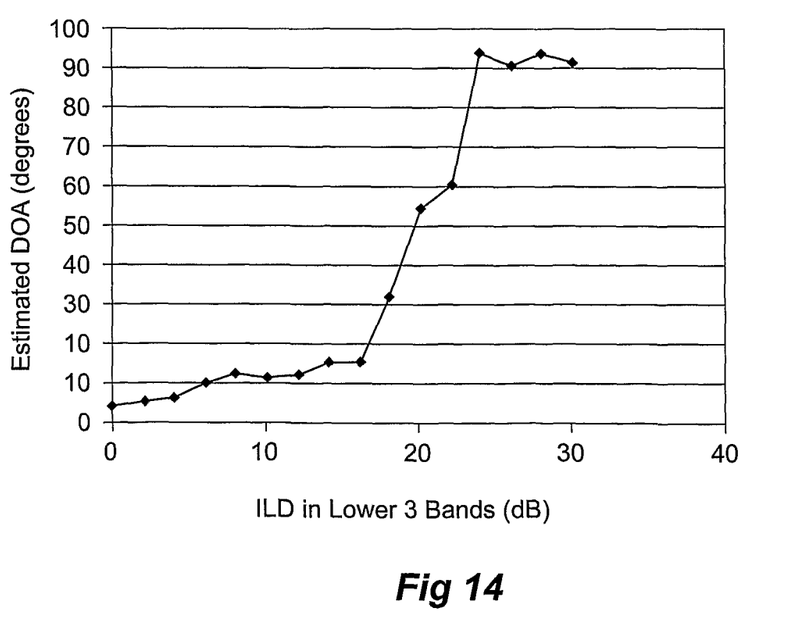
FIG. 14—shows ILDs vs Estimated location in degrees in the recipient's lower 3 bands.

In this example, it is assumed that for the recipient with a bimodal system there is only residual hearing in the first 3 frequency bands and an experiment relating ILDs in those lower frequency bands to an estimated DOA led to the results as shown in FIG. 14.

From FIG. 14, it can be seen that in order to estimate an angle of 45 degrees, the recipient needs an ILD in the lower 3 frequencies of about 19 dB. In FIG. 13, it can be seen that the current signal has an ILD of zero dB in that region, meaning the recipient would place the signal (incorrectly) in the front.

Figure 15:
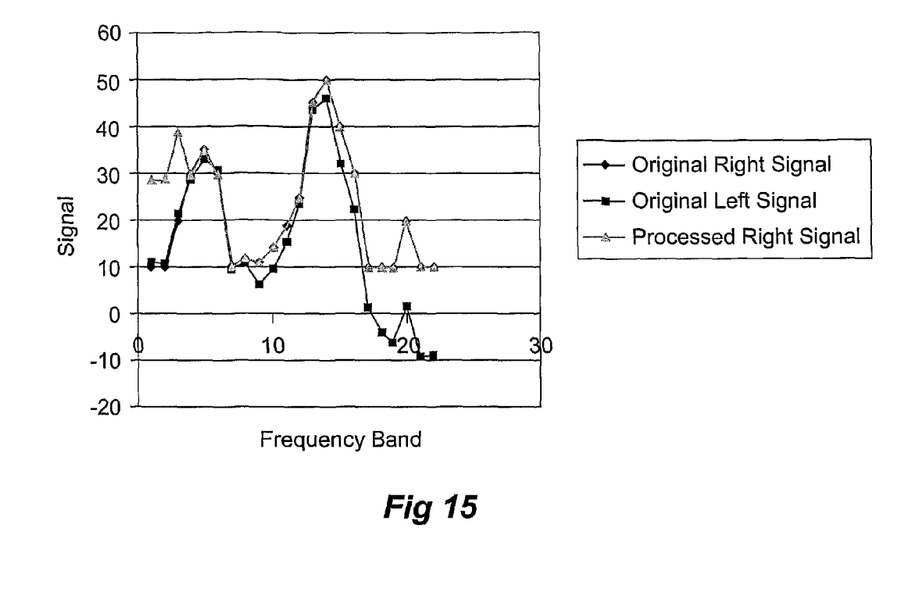
FIG. 15—shows the processed signal corrected using the ILDs.

The PostLoc block could introduce a 19 dB ILD in the signal leading to the correct estimation of the DOA by the recipient. The algorithm does this by simply adding 19 dB gain to the right device's lowest 3 frequency bands (or 19 dB attenuation to the left devices, or any combination of the two). The resulting signal will be as seen in FIG. 15.

Figure 16:
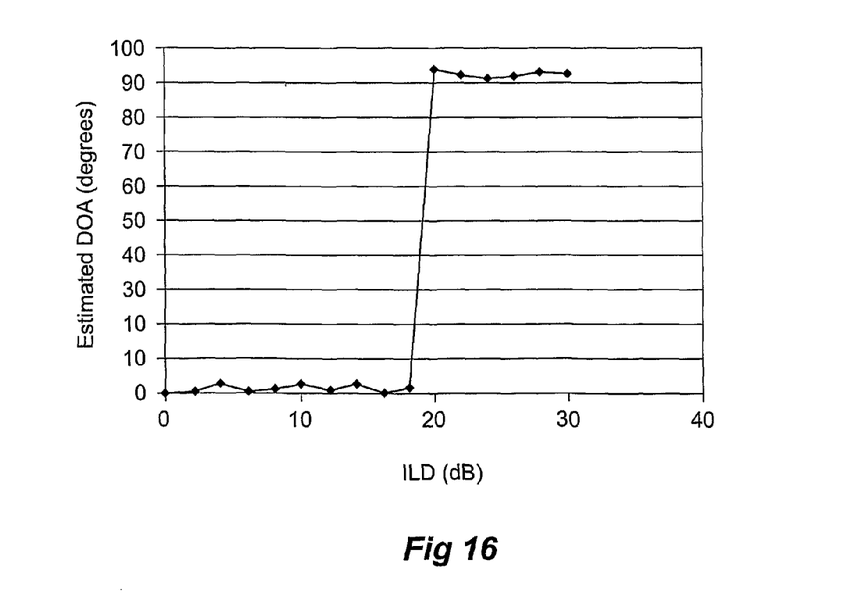
FIG. 16—shows a graph of ILDs vs Estimated location in degrees for another recipient in the lower 3 bands.

In another example, suppose that in another bilateral CI user the measuring results of FIG. 10 are as shown in FIG. 16. With the same input signal as in the previous example, this recipient will have difficulty in consistently localizing the input sound signal as the ILD was about 19 degrees which is just in the s-point of his/her curve (FIG. 16). The algorithm may introduce an ILD that is amplified to say 30 dB to enable consistent localization to the right side for this recipient.

While much of the above description has described the various aspects of the invention in the context of bilateral hearing systems, some aspects are also applicable to a unilateral recipient, i.e. a recipient having only a single hearing device.

When a single CI is used (as opposed to bilateral CI's or CI+HA), the recipient does not have access to binaural cues (ITD and ILD). Monaural cues are available, but can be distorted or attenuated due to 1) microphone placement (behind the ear, instead of in the ear), 2) compression in the CI signal processing, 3) unavailability of frequencies higher than the upper cut off frequency of the CI processor (typically around 8 khz) and 4) inability of the recipient to perceive differences between HRTFs corresponding to different sound source locations.

This can be addressed by artificially modifying HRTFs to fit them into the frequency range that is transmitted by the CI and make them perceptually distinguishable.

While at first the artificial HRTFs might not be perceived as corresponding to a certain direction, the recipient can be trained to perceive them as such (differences in HRTF are highly trainable in NH subjects).

Example 1

Consider a set of HRTFs which contain a prominent dip that shifts in frequency with changing angle of incidence (similar to the shifting dip in FIG. 3). Let the angles and dip frequencies be:

| angle (degrees) | | | | | | |
|---|---|---|---|---|---|---|
| 0 | 15 | 30 | 45 | 60 | 75 | 90 |
| freq (hertz) 12000 | 11000 | 11500 | 10000 | 9000 | 8500 | 8000 |

In this case, based on this dip, different angles can not be distinguished by the recipient because 1) frequencies above 8 kHz are not transmitted by the CI and the given differences in dip frequency might not be perceivable.

A psychophysical test may be done with the subject and it could be determined that the subject can perceive differences in dip frequency of about 500 Hz. The system could then use a tailored set of HRTFs with the following dip frequencies:

| angle (degrees) | | | | | | |
|---|---|---|---|---|---|---|
| 0 | 15 | 30 | 45 | 60 | 75 | 90 |
| freq (hertz) 8000 | 7750 | 7500 | 7250 | 7000 | 6500 | 6000 |

Note that larger angles have a better perceptual resolution. This is useful because for smaller angles there are clear visual cues to sound source location.

The system would then determine the angle of incidence of a sound source and select and apply an HRTF from the latter set based on that angle.

Example 2

To distinguish between sounds incident from the front or back, normal hearing listeners use pinna cues. These cues are typically only available at higher frequencies (>10 kHz) (which are not transmitted by the CI). A system similar to example 2 could be devised that 1) determines whether the sound came from the front or back; and 2) applies a tailored HRTF that is perceived as—or can be trained to be perceived as—corresponding to front or back.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

The invention claimed is:

1. A method comprising:
measuring a difference between a sound signal received at a first sound detector and a second sound detector;
determining a localization cue based on the measured difference;
altering the determined localization cue;
generating a first stimulation signal for application to a hearing prosthesis recipient via a first hearing prosthesis; and
generating a second stimulation signal for application to the recipient via a second hearing prosthesis, wherein the first and second hearing prostheses are different types of hearing prostheses worn by the recipient, and wherein the first and second stimulation signals are based at least in part on the altered localization cue.

2. The method of claim 1, wherein the first sound detector is associated with the first hearing prosthesis, wherein the second sound detector is associated with the second hearing prosthesis, and wherein measuring the difference between the sound signal received at the first and second sound detectors comprises:
determining energy in a sub-band of the sound signal over a time period via a processor at the second hearing prosthesis; and
sending an indication of the determined energy from the second hearing prosthesis to the first hearing prosthesis.

3. The method of claim 1, wherein determining a localization cue based on the measured difference comprises:
determining a Direction of Arrival (DOA) of the sound signal based on the measured difference; and
selecting a localization cue from a first lookup table comprising a set of localization cues, wherein individual localization cues in the first lookup table have a corresponding DOA.

4. The method of claim 1, wherein determining a localization cue based on the measured difference comprises:
comparing the measured difference with a Head Related Transfer Function (HRTF) of the recipient.

5. The method of claim 1, wherein altering the determined localization cue comprises amplifying the determined localization cue.

6. The method of claim 1, wherein altering the determined localization cue comprises frequency shifting the determined localization cue.

7. The method of claim 1, wherein altering the determined localization cue comprises amplifying and frequency shifting the determined localization cue.

8. The method of claim 1, wherein the determined localization cue is an interaural time difference (ITD), and wherein altering the determined localization cue comprises representing the ITD as an interaural level difference (ILD).

9. The method of claim 1, wherein the determined localization cue is an ILD, and wherein altering the determined localization cue comprises representing the ILD as an ITD.

10. The method of claim 1, wherein the altered localization cue comprises a binary indication.

11. The method of claim 1, wherein generating the second stimulation signal comprises:
sending instructions for generating the second stimulation signal based at least in part on the altered localization cue from the first hearing prosthesis to the second hearing prosthesis; and
generating the second stimulation signal by the second hearing prosthesis based at least in part on the instructions received from the first hearing prosthesis.

12. The method of claim 1, wherein the first and second hearing prostheses are any of a cochlear implant configured to provide electrical stimulation signals, a hearing aid configured to provide acoustic stimulation signals, a direct acoustic cochlear stimulation system configured to provide mechanical stimulation signals, a bone-anchored hearing aid configured to provide mechanical stimulation signals, a hybrid prosthesis configured to provide mechanical and acoustic stimulation signals, a hybrid prosthesis configured to provide acoustic and electrical stimulation signals, and a hybrid prosthesis configured to provide mechanical and electrical stimulation signals.

13. A system comprising:
a first hearing prosthesis comprising (i) one or more processors configured to (a) measure a difference between a sound signal received at two sound detectors, (b) determine a location cue based on the measured difference, and (c) determine one or more replacement location cues based on the determined location cue, and (ii) an output configured to generate a first stimulation signal based on at least one of the replacement location cues; and a second hearing prosthesis comprising (i) one or more processors and (ii) an output configured to generate a second stimulation signal based on at least one of the replacement location cues, wherein the first and second hearing prostheses are different types of hearing prostheses worn by a recipient.

14. The system of claim 13, wherein the one or more processors of the second hearing prosthesis are further configured to measure energy in one or more sub-bands of the sound signal over a time period, and wherein the second hearing prosthesis further comprises a transmitter configured to transmit an indication of the measured energy to the first hearing prosthesis.

15. The system of claim 13, wherein the first hearing prosthesis further comprises:
one or more lookup tables for associating individual determined location cues with one or more corresponding replacement location cues; and
wherein the first hearing prosthesis is configured to select one or more corresponding replacement location cues from the one or more lookup tables based on the determined location cue.

16. The system of claim 13, wherein the one or more processors of the first hearing prosthesis are further configured to identify spectrally-distributed ILDs that follow a Head Related Transfer Function (HRTF) of the recipient.

17. The system of claim 13, wherein the at least one replacement location cue has a greater amplitude than its corresponding determined location cue.

18. The system of claim 13, wherein the at least one replacement location cue has a different frequency than its corresponding determined location cue.

19. The system of claim 13, wherein the at least one replacement location cue has a different amplitude and frequency than its corresponding determined location cue.

20. The system of claim 13, wherein the determined location cue is an ITD, and wherein the at least one replacement location cue is an ILD based on the determined ITD.

21. The system of claim 13, wherein the determined location cue is an ILD, and wherein the at least one replacement location cue is an ITD based on the determined ILD.

22. The system of claim 13, wherein the at least one replacement location cue comprises a binary signal based on the determined location cue.

23. The system of claim 13,
wherein the first hearing prosthesis further comprises a transmitter configured to send instructions for generating the second stimulation signal based on the at least one of the replacement location cues to the second hearing prosthesis; and
wherein the second hearing prosthesis further comprises a receiver configured to receive the instructions from the first hearing prosthesis.

24. The system of claim 13, wherein the first and second hearing prostheses are any of a cochlear implant configured to provide electrical stimulation signals, a hearing aid configured to provide acoustic stimulation signals, a direct acoustic cochlear stimulation system configured to provide mechanical stimulation signals, a bone-anchored hearing aid configured to provide mechanical stimulation signals, a hybrid prosthesis configured to provide mechanical and acoustic stimulation signals, a hybrid prosthesis configured to provide acoustic and electrical stimulation signals, and a hybrid prosthesis configured to provide mechanical and electrical stimulation signals.

* * * * *